United States Patent [19]
Jacobs et al.

[11] Patent Number: 6,113,945
[45] Date of Patent: *Sep. 5, 2000

[54] MULTI-COLORED MEDICAMENT

[75] Inventors: Richard L. Jacobs, Portage; Shirish A. Shah, Kalamazoo, both of Mich.

[73] Assignee: L. Perrigo Company, Allegan, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/606,647

[22] Filed: Feb. 26, 1996

[51] Int. Cl.[7] ............................. A61K 9/28; A61K 9/48; A61K 9/64
[52] U.S. Cl. ......................... 424/474; 424/478; 514/853
[58] Field of Search ................... 424/474, 478; 514/853

[56] References Cited

U.S. PATENT DOCUMENTS

| | | |
|---|---|---|
| 2,373,721 | 4/1945 | Taylor et al. . |
| 3,185,626 | 5/1965 | Baker . |
| 3,981,984 | 9/1976 | Signorino ............................ 424/480 |
| 4,034,035 | 7/1977 | Schwartz et al. ..................... 264/77 |
| 4,133,290 | 1/1979 | Melliger ............................... 118/668 |
| 4,274,830 | 6/1981 | Woznicki et al. ........................ 8/495 |
| 4,636,261 | 1/1987 | Heinze ................................. 106/402 |
| 4,725,441 | 2/1988 | Porter et al. ........................ 424/479 |
| 4,820,524 | 4/1989 | Berta ................................. 424/474 |
| 4,867,983 | 9/1989 | Berta . |
| 4,966,771 | 10/1990 | Berta . |
| 5,089,270 | 2/1992 | Hampton et al. . |
| 5,146,730 | 9/1992 | Sadek et al. ........................... 53/454 |
| 5,188,688 | 2/1993 | Boardman et al. ..................... 156/69 |
| 5,213,738 | 5/1993 | Hampton et al. . |
| 5,228,916 | 7/1993 | Berta ................................... 118/30 |
| 5,317,849 | 6/1994 | Sauter . |
| 5,405,642 | 4/1995 | Gilis et al. ........................ 427/2.23 |
| 5,415,868 | 5/1995 | Smith et al. ......................... 424/454 |
| 5,436,026 | 7/1995 | Berta ............................... 427/2.14 |
| 5,459,983 | 10/1995 | Sadek et al. .......................... 53/560 |
| 5,464,631 | 11/1995 | Hoover et al. ....................... 424/454 |
| 5,824,338 | 10/1998 | Jacobs et al. ........................ 424/460 |

OTHER PUBLICATIONS

Physicians Desk Reference, 36th Edition. Published by Medical Economics Co., Inc. 1982. Product Identification at pp. 403–440.

*Primary Examiner*—Robert H. Harrison
*Attorney, Agent, or Firm*—Price, Heneveld, Cooper, DeWitt & Litton

[57] ABSTRACT

The medicament of the present invention and its process of manufacturing employs a caplet or tablet core with a clear or single color uniform covering which can be applied either through an enrobing process, by spraying or by a single dip-coating step. The core itself can have a first color or be colorless, and its clear or single color covering has the outer surface of one end or one side colored by a suitable dye to provide a two-color appearance. The dye can be applied by dipping or spray painting with a suitable jet-spraying apparatus. In a preferred embodiment, the covering is of a clear gelatinous material.

17 Claims, 3 Drawing Sheets

MULTI-COLORED MEDICAMENT

BACKGROUND OF THE INVENTION

The present invention relates to a medicament in the form of a caplet or tablet core which is covered with material to facilitate swallowing and subsequently at least partially colored to provide a multiple colored medicament.

Capsules have long been recognized as a preferred form of medicament for the delivery of active ingredients which may be in the form of powder, liquid or granules of different compositions, including ingredients which react at different times within the patient's body for providing sustained medical effects.

In view of the tamperability of conventional capsules made with hard shell capsule halves of different diameters which can be taken apart, steps have been taken including the belly banding of capsule halves to reduce the possibility of tampering. Although the sealing of capsule shell halves or belly banding of capsule shell halves has, in a large part, proven effective to either prevent tampering or at least make tampering evident to the consumer, some companies have preferred to manufacture solid dosage forms which are coated with gelatin as opposed to the conventional capsule dosage form. U.S. Pat. Nos. 5,089,270; 5,213,738; 4,820,524; 4,867,983 and 4,966,771 represent different approaches to providing a capsule-shaped product in the form of a caplet having a coating which provides the appearance and, therefore, the consumer acceptability of the previously popular capsule.

U.S. Pat. Nos. 5,415,868 and 5,317,849 disclose different manners by which either hard shell capsule halves can be shrink-wrapped onto a caplet (the '868 patent) or a caplet core covered at opposite ends with a soft gelatin capsule shell half and subsequently dried to simulate a capsule-like medicament (the '849 patent). U.S. Pat. No. 5,464,631 suggests that studies have also shown the functional importance to consumers of providing a capsule-appearing solid dosage form which is multi-colored. The utilization of two colors functionally identifies the type of medication as well as provides a capsule-appearing product with a psychologically perceived medicinal efficacy. Aesthetically, also, consumers apparently prefer the attractive appearance of multi-colored capsules over single colored capsules.

Thus, there has been a rush by the pharmaceutical industry to provide over-the-counter caplet dosage forms which simulate the appearance of capsules and which have a variety of multiple colors which identify the type of medication provided so that the consumer can readily identify, for example, if the product is a particular type of analgesic or whether it includes antihistamines or other active ingredients in combination with analgesics. Such solid dosage forms have preferably been in the shape of a caplet and are identified as gelcaps when a solid caplet core is covered with a gelatin covering or geltabs where the core is in the shape of a conventional tablet with a gelatin coating.

Although the above noted patents teach different approaches to providing the consumer with a capsule-appearing medicament, they do so only at the significant expense in specialized manufacturing equipment and/or manufacturing processes.

SUMMARY OF THE PRESENT INVENTION

The medicament of the present invention and its process of manufacturing overcomes the difficulty encountered with the somewhat costly machinery and processes required in the caplet and tablet manufacturing process of the prior art by providing a conventional caplet or tablet core with a clear or single colored covering which can be applied either through an enrobing process, by spraying, or a single dip-coating step to provide a uniform covering over the core. The core, which itself can have a first color and a clear covering then can have one end or side either dipped in or sprayed with a suitable dye to provide the desired two-color appearance. The resultant medicament is easy to swallow and has the desired functional multi-colored appearance.

Medicaments embodying the present invention, therefore, comprise a solid core having a clear covering of substantial uniform thickness and having one end and/or side colored with a color different than that of the core color. Methods of manufacturing the present invention include the steps of forming a medicament core, covering the core with a substantially uniform coating of clear or single colored material, coloring the outer surface of one end or side of the core and subsequently curing the coloring agent to complete the manufacturing process. In a preferred embodiment of the invention, clear or single colored gelatin is the preferred covering material.

In view of the existence of conventional tablet and caplet manufacturing machines and gelatin covering equipment, the medicament manufactured according to the present invention can be relatively inexpensively made and only requires the additional step of coloring one end or side of the medicament also utilizing existing equipment. As a result, either a multi-colored capsule-appearing solid dosage form or multi-colored tablet dosage form having the desired characteristics can be made at a reduced cost.

These and other features, objects and advantages of the present invention will become apparent upon reading the following description thereof together with reference to the accompanying drawings.

DETAILED DESCRIPTION OF THE PREFERRED EMBODIMENT

Figure 1:
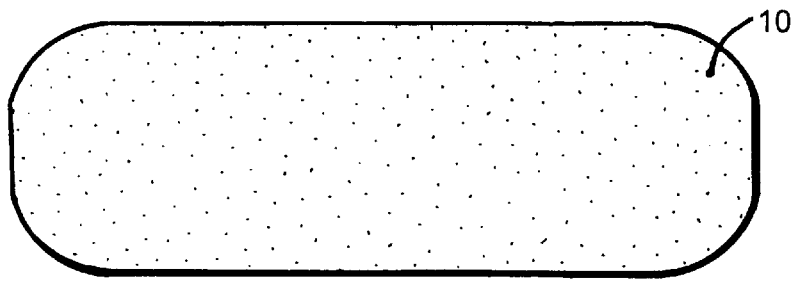
FIG. 1 is an enlarged vertical cross-sectional view of a caplet core employed in the manufacturing of a medicament embodying the present invention.
Figure 2:
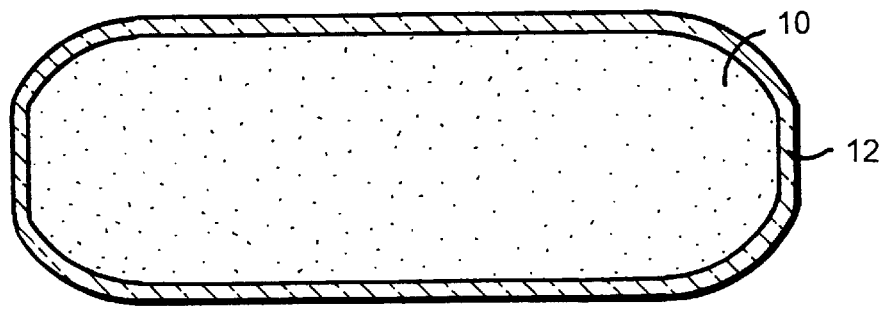
FIG. 2 is a vertical cross-sectional view of the caplet core of FIG. 1 shown with a clear or single color cover.
Figure 3:
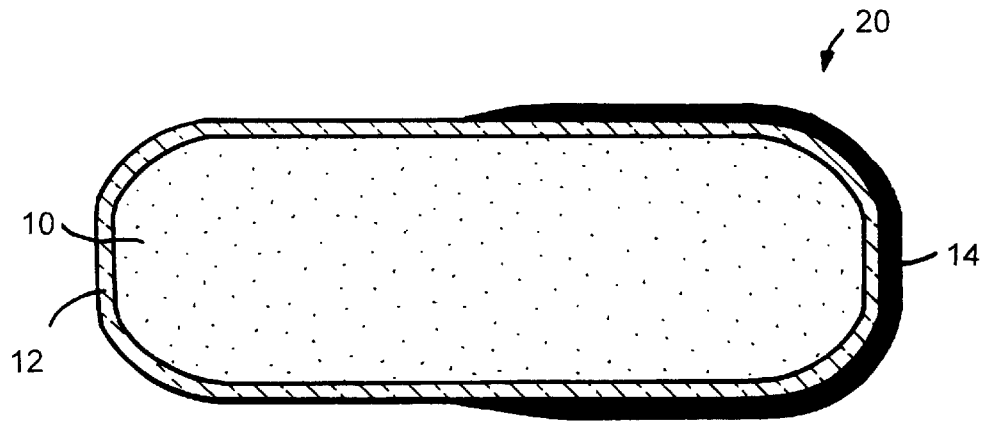
FIG. 3 is a vertical cross section of the covered caplet shown in FIG. 2 with one end colored to complete the medicament of one embodiment of the present invention.

Referring initially to FIGS. 1–3, there is shown in FIG. 1 a caplet core 10 of the capsule-shaped but solid medicament 20 (FIG. 3) of the present invention. Core 10 is pressed of a blend of suitable active ingredients and excipients which may be either their natural color, including white, or can be conventionally colored as desired to provide a conventional, caplet-shaped core of any desired color. The active ingredients may be any analgesic such as acetylsalicylic acid, acetaminophen, ibuprofen, or any other NSAID which are commonly known and which can be pressed into the shape of a caplet utilizing conventional existing tableting equipment and processes. The caplet core 10 may include other active ingredients such as antihistamines or a combination of analgesics and antihistamines or other ingredients as is conventional.

The caplet core 10 is subsequently covered with a clear covering 12 which can be any number of medicinally acceptable coverings such as gelatin, "POVIDONE®" (a 1-ethenyl-2-pyrrolidinone polymer or 1-vinyl-2-pyrrolidinone polymer), "OPADRY®" (a dry concentrate polymer and plasticizer), methyl-cellulose or other clear, film-forming material which increases the swallowability of the caplet by providing a slippery covering to easy the physical swallowing process and also masking the taste of the ingredients contained in the caplet core 10. Preferably, the covering 12 is a gelatinous covering which has a thickness of from about 0.002 inches to about 0.010 inches and can be provided either by dipping the caplet 10 in a bath of clear gelatin as taught, for example, in U.S. Pat. No. 2,373,721 and subsequently drying the covered caplet; by spray or pan covering the caplet in a conventional manner, or by an enrobing process as disclosed in U.S. Pat. No. 5,146,730, the disclosure of which is incorporated herein by reference. The covering of the caplet core 10 and the subsequent drying of the combined core 10 and clear covering 12 is conventional and well-known to those skilled in the pharmaceutical art. The color of the core is thus exposed through the clear film or covering 12. The exact equipment and processes will vary depending upon the clear covering material 12 employed. In some embodiments, the covering material such as gelatin can be pigmented in any desired single color by conventional means known to those in the art. In such a case, the end or side of the covered medicament is colored as described below with a contrasting color on the outer surface of this cover.

Subsequent to the covering of the caplet 10 as shown in FIG. 2, one end of the now covered caplet core is colored with a coloring agent 14 as seen in FIG. 3 to complete the medicament 20. The coloring 14 may be a suitable ink (or dye) of a color different than that of the caplet core 10 when a clear covering is employed or different than the single color of the cover when pigmented. In the preferred embodiment, a commercially available ink from the Colorcon Division of Berwind Pharmaceutical Services, Inc. was employed. The ink employed conventionally includes excipients to improve adhesion of ink to the gelatin covering and a pharmaceutical glaze or shellac to decrease rub-off of the ink employed. One such ink included a mixture of water, hydroxypropyl cellulose, isopropyl alcohol, FD&C red #40, simethicone, propylparaben and methylparaben for a red ink. For other colors, different coloring agents are employed to color the outer surface of the medicament. For purposes of coloring one end of the caplet, collets are employed to hold the caplets with one end exposed. The caplets are then dipped in the ink which has a viscosity of approximately 20 centipoise. If desired, the now colored end 14 and opposite end of the medicament 20 could be further covered by dipping into a tray of Opagloss®, a pharmaceutical shellac, if desired or could be sprayed using a conventional spray gun from Spraymation, Inc., although such additional covering is not necessary.

Figure 4:
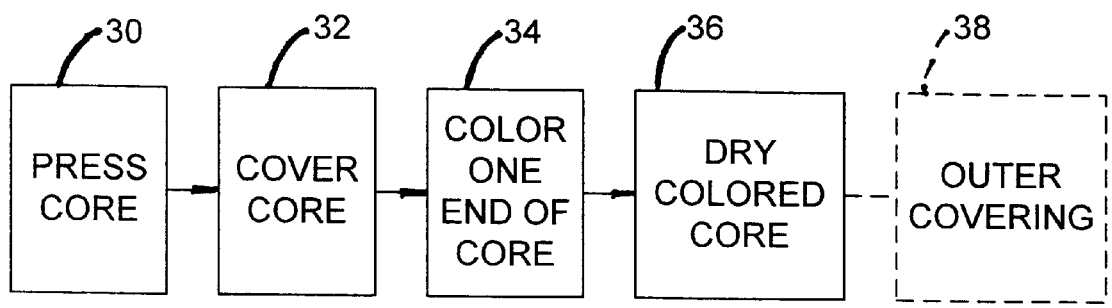
FIG. 4 is a flow diagram of the process of manufacturing the caplet shown in FIGS. 1–3 or the tablet shown in FIGS. 5–7.

The process of manufacturing the medicament 20 is illustrated in FIG. 4. The first step 30 of which is the pressing of the caplet or tablet core depending upon the desired shape of the medicament. The core is subsequently covered by the desired pharmaceutically acceptable covering, such as gelatin, as indicated by step 32 utilizing dipping, enrobing or spraying and subsequently one end or side of the core is colored as indicated by step 34. The coloring step for caplets involves inserting one end of the caplet-shaped cores into collets and immersing the exposed end into the colored ink utilizing a dipping collet such as illustrated in U.S. Pat. No. 4,867,983. The now covered and colored core is subsequently dried as indicated by step 36 which, in the preferred embodiment, was in an oven controlled to a temperature up from about 26 to 30 degrees centigrade for a period of approximately 15 minutes. If desired and as indicated in block 38 in phantom form, the medicament 20 can subsequently be over-coated with a pharmaceutical shellac such as Opagloss®, which can be sprayed or dipped over the medicament as desired, followed by a second drying step. This additional covering step may or may not be necessary or desirable depending upon the selection of dyes or inks employed.

Figure 5:
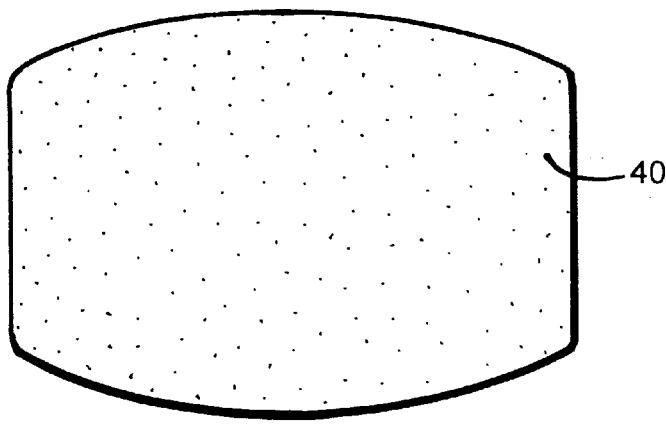
FIG. 5 is an enlarged vertical cross-sectional view of a tablet core employed in manufacturing a medicament of an alternative embodiment of the present invention.
Figure 6:
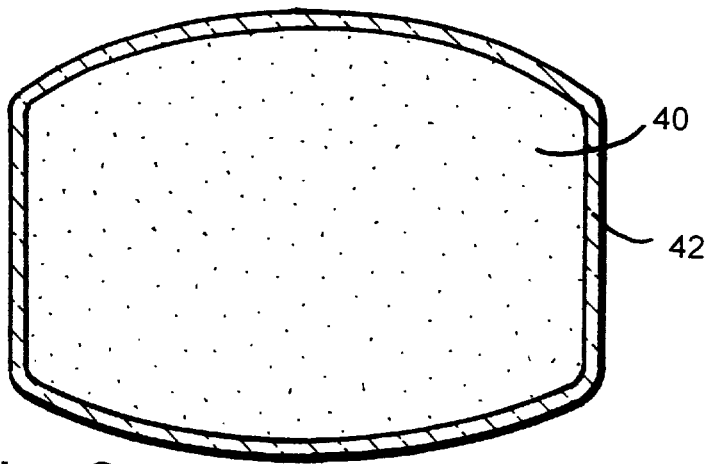
FIG. 6 is a vertical cross-sectional view of the tablet core shown in FIG. 5 covered with a clear or single color covering.
Figure 7:
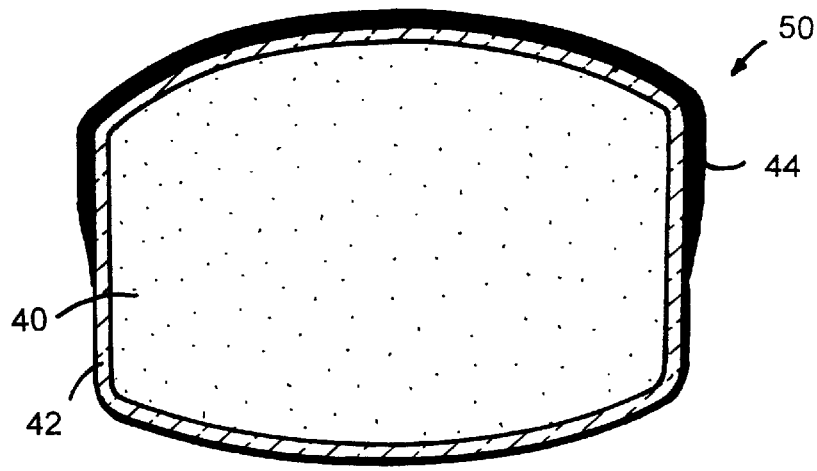
FIG. 7 is the covered tablet core shown in FIG. 6 having one side colored.

Referring now to FIGS. 5–7 in place of the capsule-shaped medicament 20 of the first embodiment of the invention, the invention may also be employed to provide a tablet-shaped medicament 50 as shown in FIGS. 5–7. Beginning with a conventional tablet-shaped core 40 as shown in FIG. 5, which again is pressed utilizing a conventional tableting press, and a blend of excipients and active ingredients to provide an analgesic, antihistamines or combinations of analgesics, antihistamines and other medication in a conventional manner. The tablet-shaped core 40 may be the natural color of the ingredients or can be colored in a conventional manner to any desired color, such as yellow, blue, green, red or different shades thereof, as is conventional. The core 40 is then covered as indicated by layer 42 by a clear or single color film covering such as gelatin, Opadry® or other conventional flavor masking, swallowability enhancing material commonly employed in the pharmaceutical industry for covering the tablets. The coating 42 preferably is a coating of gelatin which is provided by either an enrobing process as disclosed in the above identified U.S. Pat. No. 5,146,730 or can be conventionally applied by dipping the core 40 in a bath of gelatin and subsequently drying the same or by a conventional pan spraying process. Subsequently, the covered tablet shape has the outer surface of one side 44 colored with a coloring agent such as an ink or other suitable non-gelatinous paint as identified above. For such purpose, the tablet can be held utilizing a vacuum holding structure such as disclosed in U.S. Pat. No. 2,373,721 or by spraying the coloring agent 44 onto the side of the tablet to provide a dual-color appearance. Popular color combinations have included blue and white, green and white, red and yellow, white and red and other color combinations signifying the active ingredients of the tablet. Tablet 50, as shown in FIG. 7, is manufactured by the same sequence of processing steps shown in FIG. 4 and may include a subsequent outer covering of a pharmaceutically acceptable shellac as indicated by step 38.

The medicaments manufactured according to the present invention, therefore, provide the desired shape, swallowability and appearance for a solid dosage form which substantially eliminates the tamperability of the medicament. The products manufactured according to the process of this invention can be relatively inexpensively made by the use of conventional equipment and utilizing existing materials. As a result, a high quality medicament which is essentially tamper-proof and which is aesthetically and functionally acceptable to consumers is provided at a relatively reduced cost.

It will become apparent to those skilled in the art that various modifications to the preferred embodiments of the invention can be made by those skilled in the art without departing from the spirit or scope of the invention as defined by the appended claims.

The embodiments of the invention in which an exclusive property or privilege is claimed are defined as follows:

1. A multi-colored medicament comprising:
   a core having a first color for presenting said first color to the medicament;
   a seamless covering film enveloping the entire outer surface of said core and having an outer surface, said covering film allowing said first color of said core to be visible therethrough; and
   a coloring agent of a second color coating one end of said outer surface of said unitary covering film on said core.

2. The medicament as defined in claim 1, wherein said core is in the shape of a tablet.

3. The medicament as defined in claim 1, wherein said core is in the shape of a caplet.

4. The medicament as defined in claim 1, wherein said covering film includes gelatin.

5. The medicament as defined in claim 4, wherein said covering film has a thickness of from about 0.002 to about 0.010 inches.

6. The medicament as defined in claim 1, wherein said covering film is clear to expose said first color of said core.

7. The medicament as defined in claim 1, wherein said coloring agent covers about half of said covering film.

8. The medicament as defined in claim 1, wherein said core contains an active ingredient including at least one of an analgesic and an antihistamine.

9. A multi-colored medicament comprising:
   a core having a first color for presenting said first color to medicament, said core having a first end, a second end, and a longitudinal axis between said first end and said second end and having a center;
   a uniform covering film enveloping the entire outer surface of said core, and having an outer surface; and
   a coloring agent having a second color and covering about half of said covering film, said coloring agent starting at said first end and ending at about said center of said longitudinal axis.

10. The medicament as defined in claim 9, wherein said core is in the shape of a tablet.

11. The medicament as defined in claim 9, wherein said core is in the shape of a caplet.

12. The medicament as defined in claim 9, wherein said covering film includes gelatin.

13. The medicament as defined in claim 12, wherein said covering film has a thickness of from about 0.002 to about 0.010 inches.

14. The medicament as defined in claim 9, wherein said covering film is clear to expose said first color of said core.

15. A multi-colored medicament comprising:
   a core having a first end, a second end, and a longitudinal axis with a center;
   a seamless uniform covering film of a first color and presenting a first color to the medicament, said covering film enveloping the entire outer surface of said core, and having an outer surface; and
   a coloring agent of a second color on said outer surface of said covering film and coating about half of said covering film, said coloring agent starting at said first end and ending at about said center of said longitudinal axis.

16. The multi-colored medicament in claim 15, wherein said core contains an active ingredient including at least one of an analgesic and an antihistamine.

17. The multi-colored medicament in claim 15, wherein said covering film comprises gelatin.

* * * * *